United States Patent [19]

Donoghue

[11] Patent Number: 4,922,921
[45] Date of Patent: May 8, 1990

[54] DEVICE FOR TESTING ONE'S BREATH

[76] Inventor: Laurence B. Donoghue, 27225 Sunnyridge Rd., Palos Verdes, Calif. 90274

[21] Appl. No.: 931,299
[22] Filed: Nov. 17, 1986
[51] Int. Cl.⁵ .............................................. A61B 5/08
[52] U.S. Cl. .................................................. 128/717
[58] Field of Search .............. 128/717, 206.21, 206.24, 128/206.26, 206.28

[56] References Cited

U.S. PATENT DOCUMENTS

| 752,114 | 2/1904 | Sennett et al. . |
| 1,128,988 | 2/1915 | Krogmoe . |
| 1,281,211 | 10/1918 | Rogers . |
| 1,463,390 | 11/1920 | Fernandes . |
| 1,475,105 | 11/1923 | Aasen . |
| 2,009,355 | 10/1934 | Decker . |
| 2,260,701 | 10/1941 | Boothby et al. . |
| 2,281,181 | 4/1942 | Clarke . |
| 2,415,846 | 10/1944 | Randall . |
| 2,765,788 | 1/1954 | Raiche . |
| 2,780,220 | 2/1957 | Dyer ................................. 128/717 |
| 2,877,764 | 3/1959 | Galleher, Jr. . |
| 2,917,045 | 12/1959 | Schildknecht et al. . |

FOREIGN PATENT DOCUMENTS

| 1179645 | 5/1959 | France .............................. 128/717 |
| 0177393 | 3/1922 | United Kingdom . |

Primary Examiner—Angela D. Sykes
Attorney, Agent, or Firm—Nilsson, Robbins, Dalgarn, Berliner, Carson & Wurst

[57] ABSTRACT

A method of testing one's breath involving exhaling through the mouth into a face mask adapted to retain a substantial quantity of exhaled gases, and while retaining the mask in place, breathing in the exhaled gases through the nostrils.

2 Claims, 1 Drawing Sheet

DEVICE FOR TESTING ONE'S BREATH

BACKGROUND AND SUMMARY OF THE INVENTION

My invention relates to the testing of one's breath, and more particularly to a method of so doing and a device for use in performing such method.

Individuals suffering from malodorous breath normally are unaware of the situation, and thus may be offending those with whom they associate, without knowledge of the fact. The availability of a simple method to enable one to test his breath would, therefore, be something to be desired.

The present invention has for its objects to provide:
1. A novel and improved method of testing one's breath;
2. A novel and improved method of testing one's breath in a quick and simple manner;
3. A novel and improved device for use in the testing of one's breath; and
4. A novel and improved device for use in the testing of one's breath, which device is structurally quite simple and one which can be manufactured economically.

DETAILED DESCRIPTION

Figure 1:
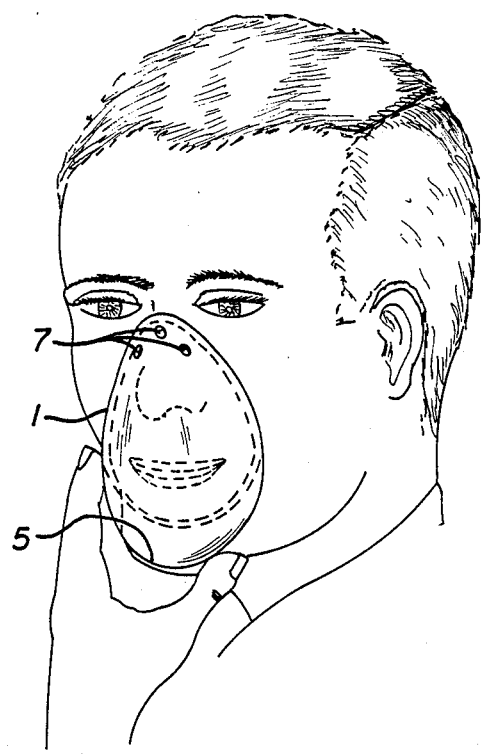
FIG. 1 is a frontal view of a mask adapted for use in carrying out the method of the present invention.
Figure 2:
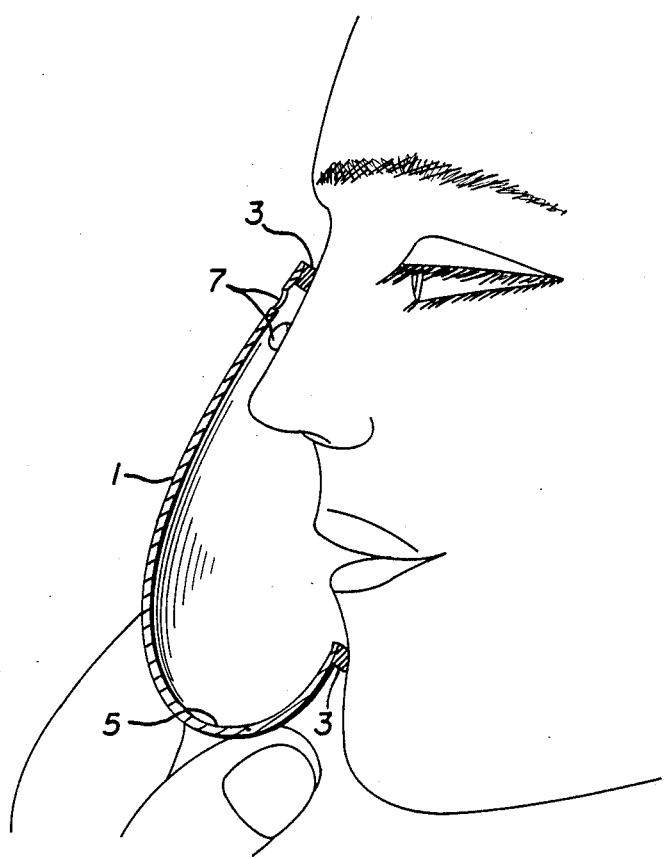
FIG. 2 is a view, in section, taken in the medial plane of the mask of FIG. 1.

Referring to the drawings for details of my method, it makes use of a face mask 1, of impervious material, such as rubber or plastic, the mask being adapted to cover one's mouth and nose, and having an edge contour adapted to sealably engage the face when the mask is held in functional position under slight pressure, and to more conveniently accomplish such sealing, an edge seal 3 of any suitable character may be installed along the edge of the mask.

For the purpose of the present method, the mask should be designed to accommodate a substantial quantity of gases as normally exhaled by an individual, with provision for a rate of escape, preferably such as to completely expel all the fresh air initially trapped within the mask. This will leave the mask filled with a quantity of the exhaled gases, which being constituted largely of heavier-than-air gases, will, in the absence of displacing pressure, tend to collect and remain in the mask, so long as the mask is retained in its sealed relationship to one's face.

To provide for such volumetric capacity as may be required for effective use of such mask in the testing of one's breath, the mask is contoured to provide a relatively deep cavity, preferably including a sump 5 below the lowest point of contact with the face.

Escape of gases from the mask may be provided for by the presence of one or more holes 7 or their equivalent, in the region of the mask lying above one's nostrils, the size and number of such openings determining the rate of escape of gases from the mask, under the varying conditions prevailing therein during a breathing cycle. In lieu of such holes, the seal may be omitted along the upper edge of the mask.

The mask is preferably and purposely devoid of any means for fastening it in position on the face, such fastening means being unnecessary since the method of its use contemplates manually supporting the mask during the brief period of use required in testing one's breath, which need not exceed but one or two breathing cycles.

Preparatory to its use, the individual takes a deep breath through the nose or mouth, either before or after applying the mask to the face, and then exhales through the mouth into the mask, causing any fresh air initially within the mask, to be expelled through the openings, thus leaving the mask full of exhaled gases, which gases, being for the most part heavier than air, will tend to remain in the mask so long as the mask is retained in position on the face.

Such retention of the mask should continue for at least the next inhaling step, which should be through the nose, whereby the individual will then be able to detect the presence of foul odors in the exhaled gases, should any exist.

Should the initial test be indecisive, one or two additional breathing cycles may be undertaken without removing the mask from the face, whereupon the gases will be reinforced by any additional malodorous gases emitted during exhaling.

From the aformentioned description of my method and the mask device for use in the performance thereof, it will be apparent that the same fulfills all the objects of my invention, and while I have disclosed and described the same in detail, it will be apparent that the same is subject to alteration and modification without departing from the underlying principles involved, and I, accordingly, do not desire to be limited in my protection to the specific details illustrated and described, except as may be necessitated by the appended claims.

I claim:

1. A device for use in testing one's breath comprising a face mask adapted to fit over the nose and mouth of a user, having an edge contoured to sealably engage the user's face under manual pressure, an upper portion of said edge formed to be disposed over the bridge of the user's nose, a lower portion of said edge formed to be disposed below and adjacent the user's lower lip, said mask having a nostril region disposed below said upper edge portion in the vicinity of the user's nostrils, said mask being formed with at least one aperture therethrough between said nostril region and said upper edge portion whereby to provide at least one air escape passageway, and a storage space sump below said lower edge portion with unobstructed direct access from said sump to said nostril region.

2. The device of claim 1 in which said face mask is formed of substantially impervious material.

* * * * *